United States Patent
Robinson et al.

(10) Patent No.: US 11,819,387 B2
(45) Date of Patent: Nov. 21, 2023

(54) COMPOSITE DRESSINGS FOR IMPROVED GRANULATION AND REDUCED MACERATION WITH NEGATIVE-PRESSURE TREATMENT

(71) Applicant: KCI Licensing, Inc., San Antonio, TX (US)

(72) Inventors: Timothy Mark Robinson, Shillingstone (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 99 days.

(21) Appl. No.: 16/000,368

(22) Filed: Jun. 5, 2018

(65) Prior Publication Data

US 2018/0353340 A1 Dec. 13, 2018

Related U.S. Application Data

(60) Provisional application No. 62/616,244, filed on Jan. 11, 2018, provisional application No. 62/615,821, filed on Jan. 10, 2018, provisional application No. 62/613,494, filed on Jan. 4, 2018, provisional application No. 62/592,950, filed on Nov. 30, 2017, provisional application No. 62/576,498, filed on Oct.

(Continued)

(51) Int. Cl.
*A61F 13/02* (2006.01)
*A61F 13/00* (2006.01)
*A61M 1/00* (2006.01)

(52) U.S. Cl.
CPC .... *A61F 13/0216* (2013.01); *A61F 13/00068* (2013.01); *A61F 13/0223* (2013.01); *A61M 1/90* (2021.05); *A61F 13/0206* (2013.01); *A61F 13/0213* (2013.01)

(58) Field of Classification Search
CPC .................................................. A61F 13/00068
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Office Action for related U.S. Appl. No. 15/997,809, dated Aug. 5, 2020.
(Continued)

*Primary Examiner* — Adam Marcetich
*Assistant Examiner* — Meagan Ngo

(57) ABSTRACT

Dressings for use in negative pressure therapy and methods of making the dressings are provided herein. The dressings may comprise at least two layers in a stacked configuration. The first layer may comprise a manifold layer and the second layer may comprise a silicone gel layer. The second layer may have perforations to form fluid restrictions that can open and close when used in negative pressure therapy. The perforated second layer may be formed by a first and a second curing step.

30 Claims, 6 Drawing Sheets

Related U.S. Application Data 24, 2017, provisional application No. 62/565,754, filed on Sep. 29, 2017, provisional application No. 62/516,550, filed on Jun. 7, 2017, provisional application No. 62/516,540, filed on Jun. 7, 2017, provisional application No. 62/516,566, filed on Jun. 7, 2017.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A | 11/1979 | Gallagher |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,983,173 A | 1/1991 | Patience et al. |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A | 5/1994 | Karami et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A | 6/1997 | Fabo |
| 5,636,643 A | 6/1997 | Argenta et al. |
| 5,645,081 A | 7/1997 | Argenta et al. |
| 5,720,714 A | 2/1998 | Penrose |
| 5,842,503 A | 12/1998 | Foley |
| 5,951,505 A | 9/1999 | Gilman et al. |
| 5,981,822 A | 11/1999 | Addison |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,278,036 B1 | 8/2001 | Anhauser et al. |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,623,681 B1 | 9/2003 | Taguchi et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |

(56) References Cited

U.S. PATENT DOCUMENTS

| | | | |
|---|---|---|---|
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1* | 2/2004 | Hunt ............... A61L 15/22 604/317 |
| 2004/0126413 A1* | 7/2004 | Sigurjonsson ........ A61L 15/26 424/445 |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2005/0226917 A1 | 10/2005 | Burton |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1 | 12/2008 | Olson et al. |
| 2009/0047495 A1 | 2/2009 | Hubbs |
| 2009/0082746 A1 | 3/2009 | Thomas et al. |
| 2009/0221979 A1 | 9/2009 | Huang et al. |
| 2009/0234307 A1 | 9/2009 | Vitaris |
| 2009/0293887 A1 | 12/2009 | Wilkes et al. |
| 2010/0030170 A1 | 2/2010 | Keller et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1 | 3/2010 | Olson |
| 2010/0069885 A1 | 3/2010 | Stevenson et al. |
| 2010/0106115 A1 | 4/2010 | Hardman et al. |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0178451 A1 | 7/2011 | Robinson et al. |
| 2011/0213287 A1 | 9/2011 | Lattimore et al. |
| 2011/0224631 A1 | 9/2011 | Simmons et al. |
| 2011/0282309 A1 | 11/2011 | Adie et al. |
| 2011/0313374 A1 | 12/2011 | Lockwood et al. |
| 2012/0046603 A1* | 2/2012 | Vinton ............ A61F 13/00051 604/24 |
| 2012/0095380 A1 | 4/2012 | Gergely et al. |
| 2012/0157945 A1 | 6/2012 | Robinson et al. |
| 2012/0209226 A1 | 8/2012 | Simmons et al. |
| 2012/0238932 A1 | 9/2012 | Atteia et al. |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1 | 2/2014 | Barberio |
| 2014/0058309 A1 | 2/2014 | Addison et al. |
| 2014/0081192 A1 | 3/2014 | Wenske et al. |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0038933 A1 | 2/2015 | Day et al. |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0119833 A1* | 4/2015 | Coulthard ......... A61F 13/00068 604/319 |
| 2015/0141941 A1 | 5/2015 | Allen et al. |
| 2015/0150729 A1 | 6/2015 | Dagger et al. |
| 2015/0174291 A1 | 6/2015 | Zimnitsky et al. |
| 2015/0174304 A1 | 6/2015 | Askem et al. |
| 2015/0290042 A1 | 10/2015 | Freer et al. |
| 2015/0290050 A1 | 10/2015 | Wada |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1 | 2/2016 | Hartwell et al. |
| 2016/0095754 A1 | 4/2016 | Andrews et al. |
| 2016/0144084 A1 | 5/2016 | Collinson et al. |
| 2016/0144085 A1 | 5/2016 | Melin et al. |
| 2016/0166744 A1* | 6/2016 | Hartwell ........... A61F 13/00021 604/319 |
| 2016/0175156 A1 | 6/2016 | Locke et al. |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |
| 2017/0079846 A1 | 3/2017 | Locke et al. |
| 2017/0095374 A1 | 4/2017 | Lauer |
| 2017/0172807 A1 | 6/2017 | Robinson et al. |
| 2017/0174852 A1 | 6/2017 | Hanschen et al. |
| 2017/0209312 A1 | 7/2017 | Kanchagar et al. |
| 2017/0258640 A1 | 9/2017 | Ahsani Ghahreman et al. |
| 2017/0312406 A1 | 11/2017 | Svensby |
| 2017/0348154 A1 | 12/2017 | Robinson et al. |
| 2017/0348158 A1 | 12/2017 | You et al. |
| 2018/0071148 A1 | 3/2018 | Lockwood et al. |
| 2018/0289872 A1 | 10/2018 | Coulthard et al. |
| 2018/0296394 A1 | 10/2018 | Barberio |
| 2019/0184075 A1 | 6/2019 | Roos |
| 2020/0282113 A1 | 9/2020 | Bengtson |

FOREIGN PATENT DOCUMENTS

| | | |
|---|---|---|
| AU | 755496 B2 | 12/2002 |
| CA | 2005436 A1 | 6/1990 |
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0174803 A2 | 3/1986 |
| EP | 0355302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2468905 A | 9/2010 |
| JP | 2008073187 A | 4/2008 |

(56) References Cited

FOREIGN PATENT DOCUMENTS

| | | |
|---|---|---|
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9319709 A1 | 10/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2007113597 A2 | 10/2007 |
| WO | 2009002260 A1 | 12/2008 |
| WO | 2010061228 A1 | 6/2010 |
| WO | 2011008497 A2 | 1/2011 |
| WO | 2011121127 A1 | 10/2011 |
| WO | 2011127188 A2 | 10/2011 |
| WO | 2011135286 A1 | 11/2011 |
| WO | 2012063725 A1 | 5/2012 |
| WO | 2014140608 A1 | 9/2014 |
| WO | 2015098373 A1 | 7/2015 |
| WO | 2015168681 A1 | 11/2015 |
| WO | 2015169637 A1 | 11/2015 |
| WO | 2015173547 A1 | 11/2015 |
| WO | 2015193257 A1 | 12/2015 |
| WO | 2016014645 A1 | 1/2016 |
| WO | 2016015001 A2 | 1/2016 |
| WO | 2017040045 A1 | 3/2017 |
| WO | 2017119996 A1 | 7/2017 |

OTHER PUBLICATIONS

Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Office Action for related U.S. Appl. No. 16/000,284, dated Jun. 8, 2020.
Office Action for related U.S. Appl. No. 15/997,833, dated Jun. 19, 2020.
3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyelhylene-Single-Sided-Medical-Tape-63-Liner/?N=5002385+8729793+3294739632&rt=rud; accessed May 21, 2019>.
3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N=5002385+4294834151&rt=d; accessed May 21, 2019>.
International Search Report and Written Opinion for related application PCT/US2018/036013, dated Aug. 7, 2018.
International Search Report and Written Opinion for related application PCT/US2018/035945, dated Aug. 24, 2018.
International Search Report and Written Opinion for related application PCT/US2018/036074, dated Aug. 24, 2018.
International Search Report and Written Opinion for related application PCT/US2018/035957, dated Sep. 28, 2018.
International Search Report and Written Opinion for related application PCT/US2018/035995, dated Oct. 1, 2018.
International Search Report and Written Opinion for related application PCT/US2018/036021, dated Aug. 24, 2018.
International Search Report and Written Opinion for related application PCT/US2018/036019, dated Oct. 18, 2018.
International Search Report and Written Opinion for related application PCT/US2018/036054, dated Aug. 24, 2018.
International Search Report and Written Opinion for related application PCT/US2018/036049, dated Aug. 29, 2018.
International Search Report and Written Opinion for related application PCT/US2018/036077, dated Aug. 24, 2018.
International Search Report and Written Opinion for related application PCT/US2018/036129, dated Oct. 8, 2018.
Heit, et al., "Foam Pore Size Is a Critical Interface Parameter of Suction-Based Wound Healing Devices," copyright 2012 by the American Society of Plastic Surgeons (www. PRSJournal.com) (Year: 2011).
Office Action for related U.S. Appl. No. 16/000,284, dated Sep. 23, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

(56) References Cited

OTHER PUBLICATIONS

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ? uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All- Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,809, dated Jan. 28, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.
Chinese Office Action for related application 201880048393X, dated May 26, 2021.
Office Action for related U.S. Appl. No. 15/997,809, dated Jul. 8, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,833, dated Mar. 26, 2021.
Office Action for related U.S. Appl. No. 16/000,215, dated Apr. 12, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.
Office action for related U.S. Appl. No. 16/000,002, dated Oct. 4, 2021.
Office Action for related U.S. Appl. No. 15/997,923, dated Nov. 16, 2021.
Office Action for related U.S. Appl. No. 16/959,651, dated Feb. 15, 2022.
Japanese Office Action for related application 2019-566886, dated Mar. 29, 2022.
Office Action for related U.S. Appl. No. 16/000,383, dated Mar. 31, 2022.
Pappas et al, "Wettability Tests of Polymer Films and Fabrics and Determination of Their Surface Energy by Contact- Angle Methods," Army Research Laboratory, ARL-TR-4056, Mar. 2007, p. 5.
Baltex, Technical Fabrics & Technical Textile Products, https://www.baltex.co.uk/products/xd-spacer-fabrics/, accessed Apr. 20, 2022.

(56) References Cited

OTHER PUBLICATIONS

Yimin Qin, Applications of Advanced Technologies in the Development of Functional Medical Textile Materials, Medical Textile Materials, 2016, pp. 55-70, Woodhead Publishing.

Baltex, Technical Fabrics & Technical Textile Products http://web.archive.org/web/20150118084138/http://www.baltex.co.uk/products/Healthcarefabrics/, 2015.

Office Action for related U.S. Appl. No. 17/204,548, dated Apr. 19, 2022.

Office Action for related U.S. Appl. No. 16/000,411, dated Jan. 31, 2022.

Office Action for related U.S. Appl. No. 15/997,818, dated Jun. 9, 2022.

Japanese Office Action for related application 2019-567267, dated Jun. 7, 2022.

Japanese Office Action for related application 2019-566969, dated Jun. 7, 2022.

Japanese Office Action for related application 2019-567266, dated Jun. 7, 2022.

Japanese Office Action for related application 2019-566908, dated Aug. 2, 2022.

Office Action for related application 15/9978333, dated Nov. 14, 2022.

Office Action for related U.S. Appl. No. 15/997,833, dated Mar. 28, 2023.

Office Action for related U.S. Appl. No. 15/997,833, dated Sep. 19, 2023.

* cited by examiner

COMPOSITE DRESSINGS FOR IMPROVED GRANULATION AND REDUCED MACERATION WITH NEGATIVE-PRESSURE TREATMENT

RELATED APPLICATION

This application claims the benefit, under 35 U.S.C. § 119(e), of the filing of U.S. Provisional Patent Application Ser. No. 62/616,244, entitled "COMPOSITE DRESSINGS FOR IMPROVED GRANULATION AND REDUCED MACERATION WITH NEGATIVE-PRESSURE TREATMENT," filed Jan. 11, 2018; U.S. Provisional Patent Application Ser. No. 62/615,821, entitled "METHODS FOR MANUFACTURING AND ASSEMBLING DUAL MATERIAL TISSUE INTERFACE FOR NEGATIVE-PRESSURE THERAPY," filed Jan. 10, 2018; U.S. Provisional Patent Application Ser. No. 62/613,494, entitled "PEEL AND PLACE DRESSING FOR THICK EXUDATE AND INSTILLATION," filed Jan. 4, 2018; U.S. Provisional Patent Application Ser. No. 62/592,950, entitled "MULTI-LAYER WOUND FILLER FOR EXTENDED WEAR TIME," filed Nov. 30, 2017; U.S. Provisional Patent Application Ser. No. 62/576,498, entitled "SYSTEMS, APPARATUSES, AND METHODS FOR NEGATIVE-PRESSURE TREATMENT WITH REDUCED TISSUE IN-GROWTH," filed Oct. 24, 2017; U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to dressings for tissue treatment with negative pressure and methods of manufacturing and using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, dressings, and methods for treating tissue in a negative-pressure therapy environment are set forth in the appended claims. Illustrative embodiments are also provided to enable a person skilled in the art to make and use the claimed subject matter.

For example, in some embodiments, dressings are provided herein for treating a tissue site with negative pressure. The dressings may comprise a first layer coupled to a second layer, wherein the second layer comprises a plurality of fluid restrictions through the second layer that are configured to expand in response to a pressure gradient across the second layer. In some embodiments, the first layer may comprise a manifold layer, and the second layer may comprise a silicone gel layer. Additionally the dressings may further comprise a cover and a release liner, and may be present in a stacked configuration.

Additionally, methods of manufacturing the dressings are also provided herein. For example, in some embodiments, a first curing step can form the second layer, for example a silicone gel layer. Then a second curing step can be performed to locally cure the second layer at desired perforation locations on the second layer. The perforated second layer can then be assembled with the first layer being interposed between a cover and the second layer in a stacked configuration Lastly, methods of treating a surface wound with negative pressure are also provided herein comprising applying the dressings described herein to a surface wound, sealing the dressing to epidermis adjacent the surface wound, fluidly coupling the dressing to a negative pressure source, and applying negative pressure from the negative pressure source to the dressing to promote healing and tissue granulation.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assumes a frame of reference consistent with or relative to a patient in a position to receive treatment. However, as should be recognized by those skilled in the art, this frame of reference is merely a descriptive expedient rather than a strict prescription.

I. Therapy Systems

Figure 1:
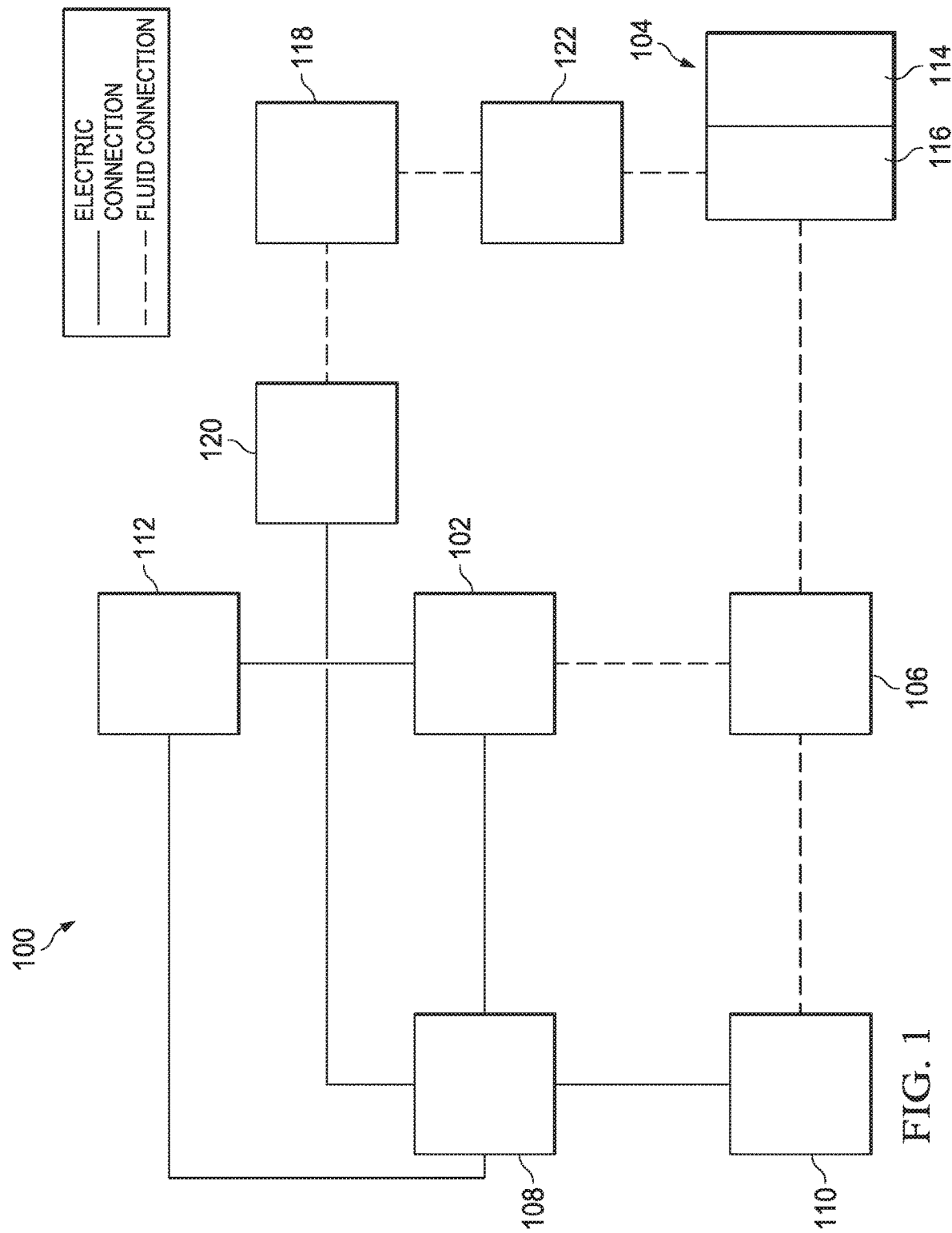
FIG. 1 is a functional block diagram of an example embodiment of a therapy system that can provide tissue treatment in accordance with this specification.

At the outset, negative pressure therapy systems are provided herein. FIG. 1 is a simplified functional block diagram of an example embodiment of a therapy system 100 that can provide negative pressure therapy to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a first sensor 110 and a second sensor 112 coupled to the controller 108.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108 and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108. The negative-pressure source maybe fluidly coupled to one or more distribution components, which provide a fluid path to a tissue site. In some embodiments, components may also be coupled by virtue of physical proximity, being integral to a single structure, or being formed from the same piece of material.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components, including sensors and data communication devices. In some embodiments, for example, a dressing interface may facilitate coupling a fluid conductor to the dressing 104. For example, such a dressing interface may be a SENSA-T.R.A.C.™ Pad available from KCI of San Antonio, Tex.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−9.9 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the first sensor 110 and the second sensor 112, are generally known in the art as any apparatus operable to detect or measure a physical phenomenon or property, and generally provide a signal indicative of the phenomenon or property that is detected or measured. For example, the first sensor 110 and the second sensor 112 may be configured to measure one or more operating parameters of the therapy system 100. In some embodiments, the first sensor 110 may be a transducer configured to measure pressure in a pneumatic pathway and convert the measurement to a signal indicative of the pressure measured. In some embodiments, for example, the first sensor 110 may be a piezo-resistive strain gauge. The second sensor 112 may optionally measure operating parameters of the negative-pressure source 102, such as the voltage or current, in some embodiments. Preferably, the signals from the first sensor 110 and the second sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

II. Dressings

In addition to therapy systems, dressings are also provided herein. As illustrated in the example of FIG. 1, the dressing 104 may comprise or consist essentially of one or more dressing layers, such as a tissue interface 114, a cover 116, or both in some embodiments.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms and have more than one layer in some embodiments. The tissue interface 114 may also have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Additionally, in some embodiments, the tissue interface 114 may be smooth, rough or matte.

Figure 2:
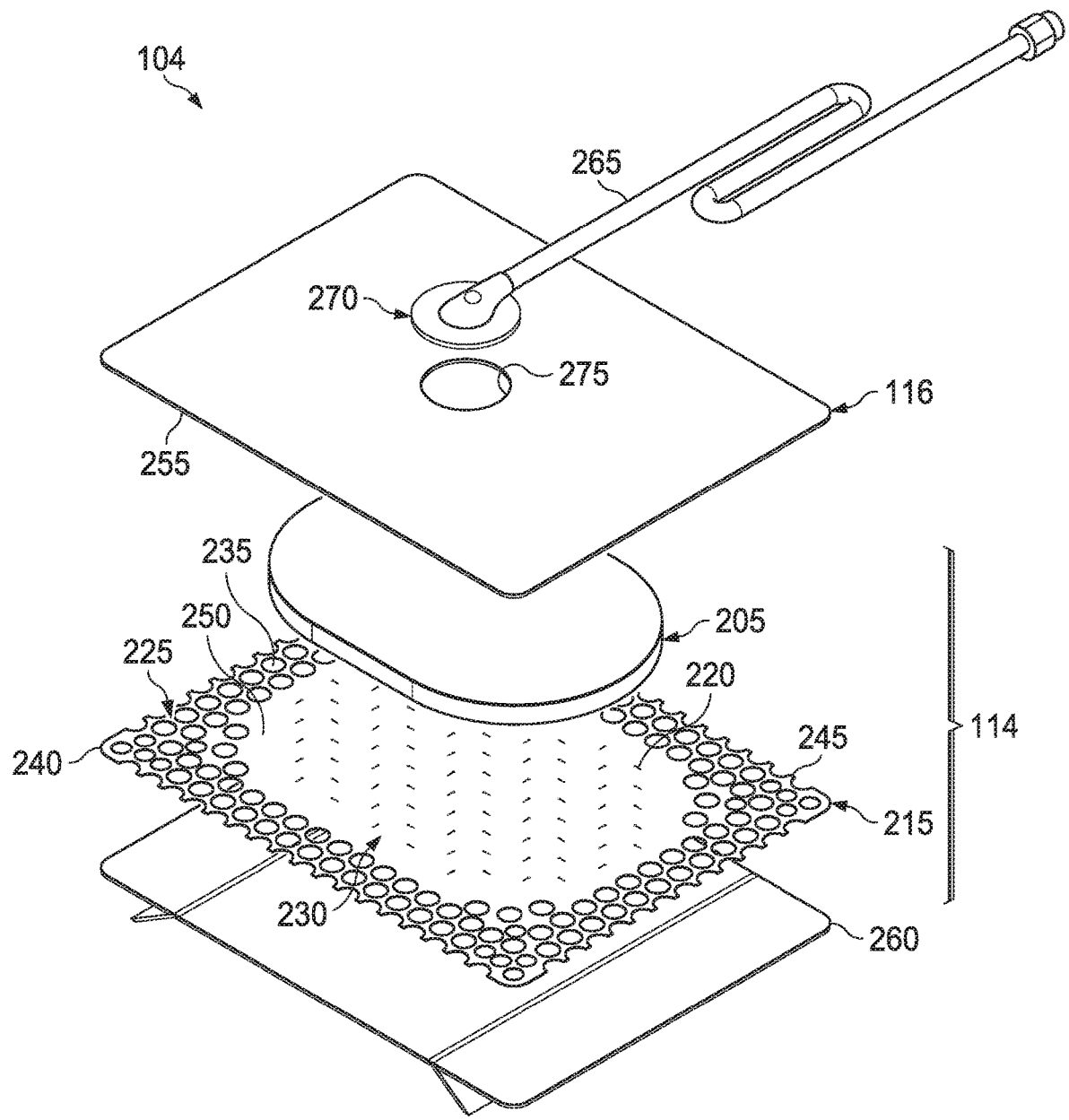
FIG. 2 is an assembly view of an example of a dressing, illustrating additional details that may be associated with some example embodiments of the therapy system of FIG. 1.

FIG. 2 is an assembly view of an example of the dressing 104 of FIG. 1, illustrating additional details that may be associated with some embodiments in which the tissue interface 114 comprises more than one layer. In the example of FIG. 2, the tissue interface 114 comprises a first layer 205 and a second layer 215. In some embodiments, the first layer 205 may be disposed adjacent to the second layer 215. For example, the first layer 205 and the second layer 215 may be stacked so that the first layer 205 is in contact with the second layer 215. The first layer 205 and the second layer 215 may also be bonded to each other in some embodiments.

A. First Layer

The first layer 205 may comprise or consist essentially of a manifold or manifold layer, which can provide a means for collecting or distributing fluid across the tissue interface 114 under pressure. For example, the first layer 205 may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 114.

In some illustrative embodiments, the first layer 205 may comprise a plurality of pathways, which can be interconnected to improve distribution or collection of fluids. In some embodiments, the first layer 205 may comprise or consist essentially of a porous material having interconnected fluid pathways. For example, open-cell foam (including reticulated foam), porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the first layer 205 may additionally or alternatively comprise projections that form interconnected fluid pathways. For example, the first layer 205 may be molded to provide surface projections that define interconnected fluid pathways. Any or all of the surfaces of the first layer 205 may have an uneven, coarse, or jagged profile.

In some embodiments, the first layer 205 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (μm) (40-50 pores per inch) may be particularly suitable for some types of therapy. The tensile strength of the first layer 205 may also vary according to needs of a prescribed therapy. For example, the tensile strength of foam may be increased for instillation of topical treatment solutions. The 25% compression load deflection of the first layer 205 may be at least 0.35 pounds per square inch, and the 65% compression load deflection may be at least 0.43 pounds per square inch. In some embodiments, the tensile strength of the first layer 205 may be at least 10 pounds per square inch. The first layer 205 may have a tear strength of at least 2.5 pounds per inch. In some embodiments, the first layer 205 is a substantially hydrophobic layer. In other embodiments, the first layer 205 is a substantially hydrophilic layer. In some embodiments, the first layer 205 may be foam comprised of polyols such as polyester or polyether, isocyanate such as toluene diisocyanate, and polymerization modifiers such as amines and tin compounds. In one non-limiting example, the first layer 205 may be a reticulated polyurethane ether foam such as used in GRANUFOAM™ dressing or V.A.C. VERAFLO™ dressing, both available from KCI of San Antonio, Tex.

The thickness of the first layer 205 may also vary according to needs of a prescribed therapy. For example, the thickness of the first layer 205 may be decreased to relieve stress on other layers and to reduce tension on peripheral tissue. The thickness of the first layer 205 can also affect the conformability of the first layer 205. In some embodiments, a thickness in a range of about 5 millimeters to about 10 millimeters may be suitable, for example about 7 millimeters.

B. Second Layer

The second layer 215 may be a sealing layer comprising or consisting essentially of a soft, pliable material suitable for providing a fluid seal with a tissue site, and may have a substantially flat surface. For example, the second layer 215 may comprise a gel layer such as, without limitation, a silicone, polyurethane, hydrocolloid, acrylic or polyolefinic gel. In some embodiments, the second layer 215 may have a thickness between about 200 microns (μm) and about 1000 microns (μm). In some embodiments, the second layer 215 may have a hardness between about 5 Shore OO and about 80 Shore OO. Further, the second layer 215 may be comprised of hydrophobic or hydrophilic materials.

In some embodiments, the second layer 215 may be present on a substrate, such as, for example, a woven, non-woven, molded, or extruded mesh, or a film.

Additionally, in some embodiments, the second layer 215 has an interior portion 230 which may correspond to a surface area of the first layer 205. The second layer 215 may also have corners 240 and edges 245. The corners 240 and the edges 245 may be part of the periphery 225. The second layer 215 may also have an interior border 250 around the interior portion 230, disposed between the interior portion 230 and the periphery 225. The interior border 250 may be substantially free of apertures 235, as shown in FIG. 2. Apertures 235 are discussed herein. Further, in some examples, as shown in FIG. 2, the interior portion 230 may be symmetrical and centrally disposed in the second layer 215.

(i) Fluid Restrictions

The second layer 215 may have a periphery 225 surrounding or around the interior portion 230; one or more fluid restrictions 220 in the interior portion 230; and apertures 235 disposed through the periphery 225. In some embodiments, the fluid restrictions 220 can be distributed uniformly or randomly across the interior portion 230. The fluid restrictions 220 may be bi-directional and responsive to pressure changes. For example, the fluid restrictions 220 can generally comprise or consist essentially of an elastic passage that is normally unstrained to substantially reduce liquid flow, and can expand in response to a pressure gradient. In some embodiments, the fluid restrictions 220 may comprise or consist essentially of perforations in the second layer 215. Perforations may be formed by removing material from the second layer 215. For example, perforations may be formed by cutting through the second layer 215, which may also deform the edges of the perforations in some embodiments. In the absence of a pressure gradient across the perforations, the passages may be sufficiently small to form a seal or flow restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the second layer 215 may be a suitable valve for some applications. Fenestrations may also be formed by removing material from the second layer 215, but the amount of material removed and the resulting dimensions of the fenestrations may be up to an order of magnitude less than perforations, and may not deform the edges.

For example, some embodiments of the fluid restrictions 220 may comprise or consist essentially of one or more slots or combinations of slots in the second layer 215. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

Figure 3:
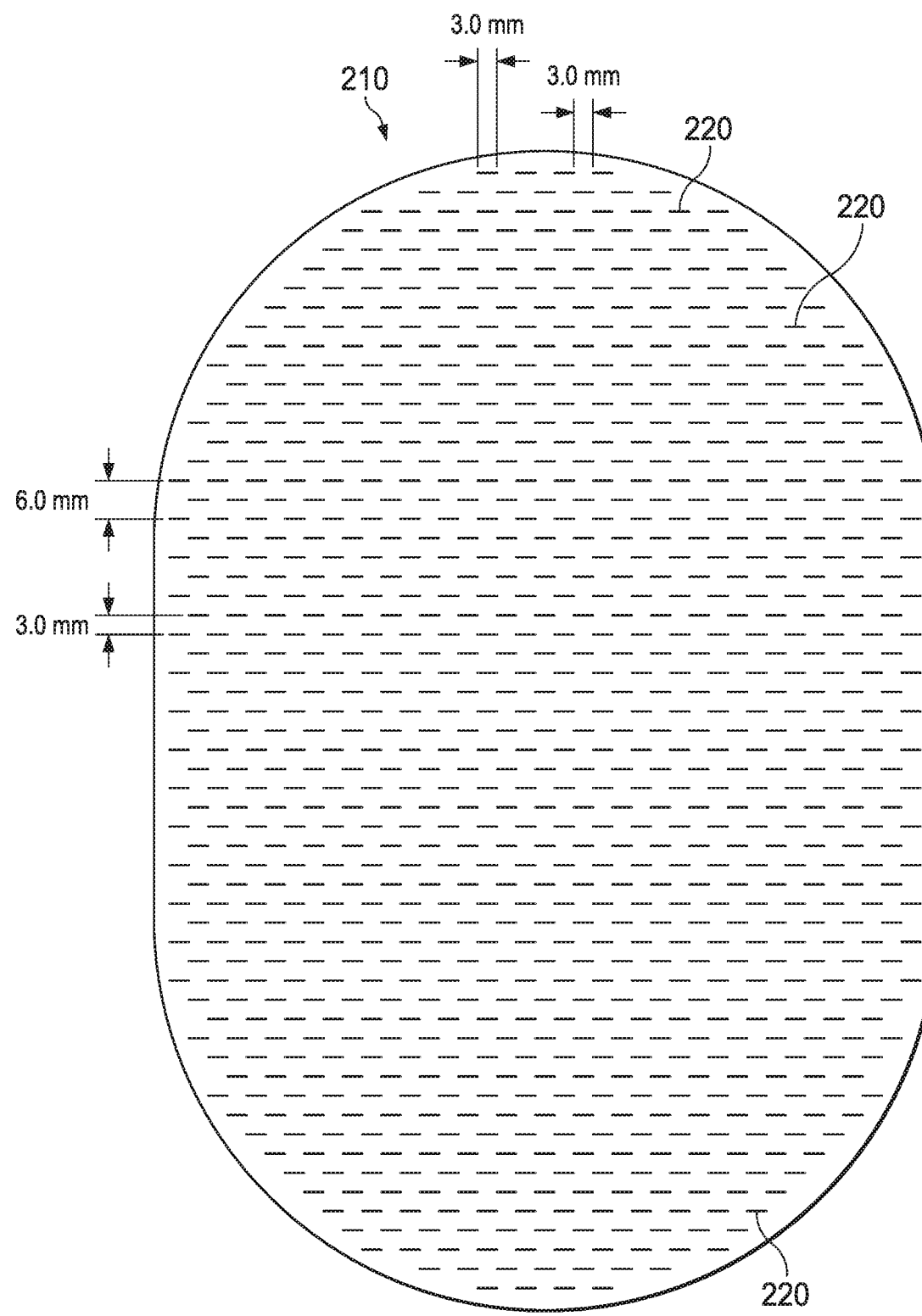
FIG. 3 is a schematic view of an example configuration of fluid restrictions in a layer that may be associated with some embodiments of the dressing of FIG. 2.

FIG. 3 is a schematic view of an example of the second layer 215, illustrating additional details that may be associated with some embodiments. As illustrated in the example of FIG. 3, the fluid restrictions 220 may each consist essentially of one or more linear slots having a length of about 3 millimeters. FIG. 3 additionally illustrates an example of a uniform distribution pattern of the fluid restrictions 220 across the second layer 215. In FIG. 3, the fluid restrictions 220 are substantially coextensive with the second layer 215, and are distributed across the second layer 215 in a grid of parallel rows and columns, in which the slots are also mutually parallel to each other. In some embodiments, the rows may be spaced about 3 millimeters on center, and the fluid restrictions 220 within each of the rows may be spaced about 3 millimeters on center as illustrated in the example of FIG. 3. The fluid restrictions 220 in adjacent rows may be aligned or offset. For example, adjacent rows may be offset, as illustrated in FIG. 3, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

Figure 4:
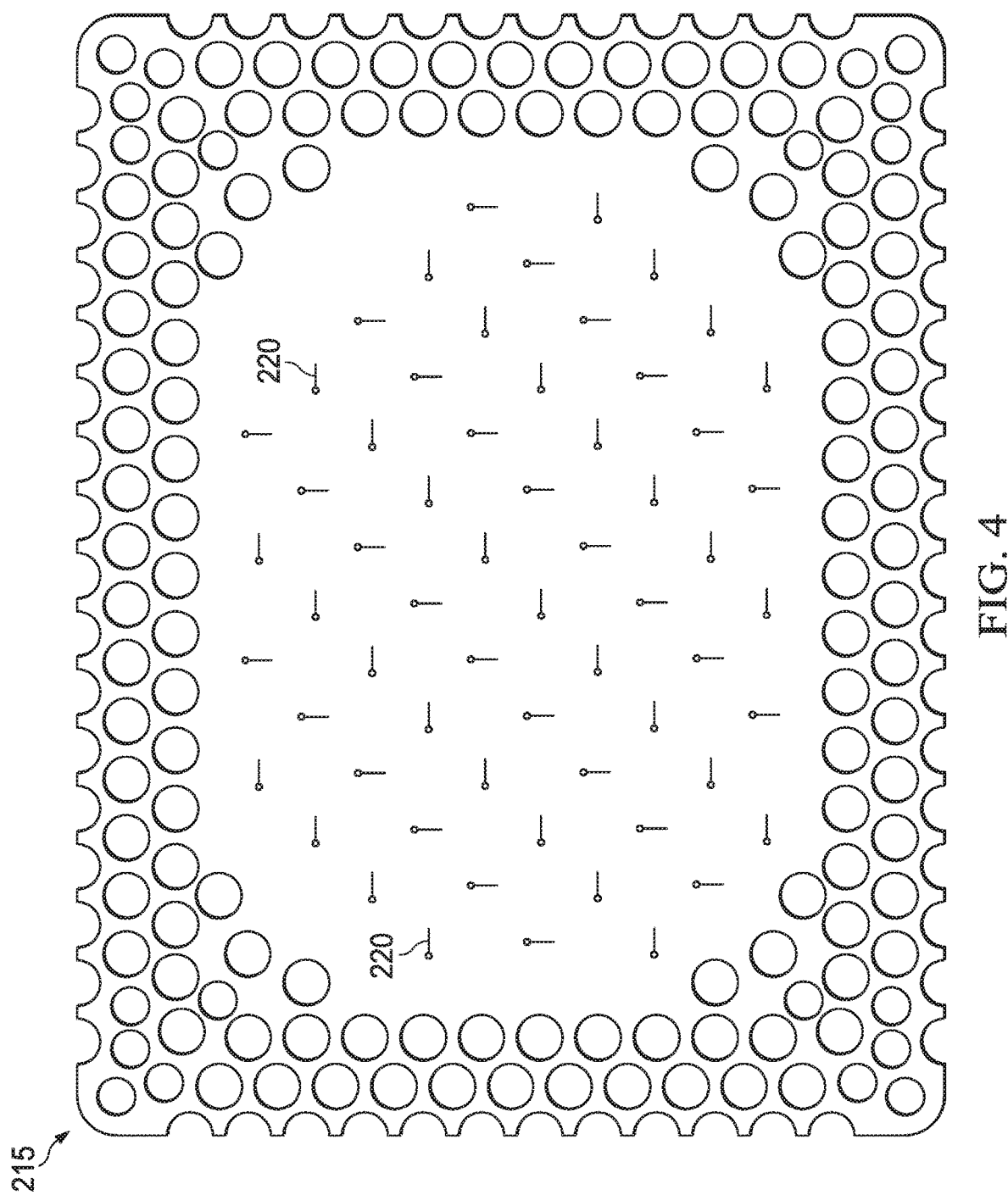
FIG. 4, FIG. 5 and FIG. 6 illustrate other example configurations of fluid restrictions that may be associated with some embodiments of layers of the dressing of FIG. 2.
Figure 5:
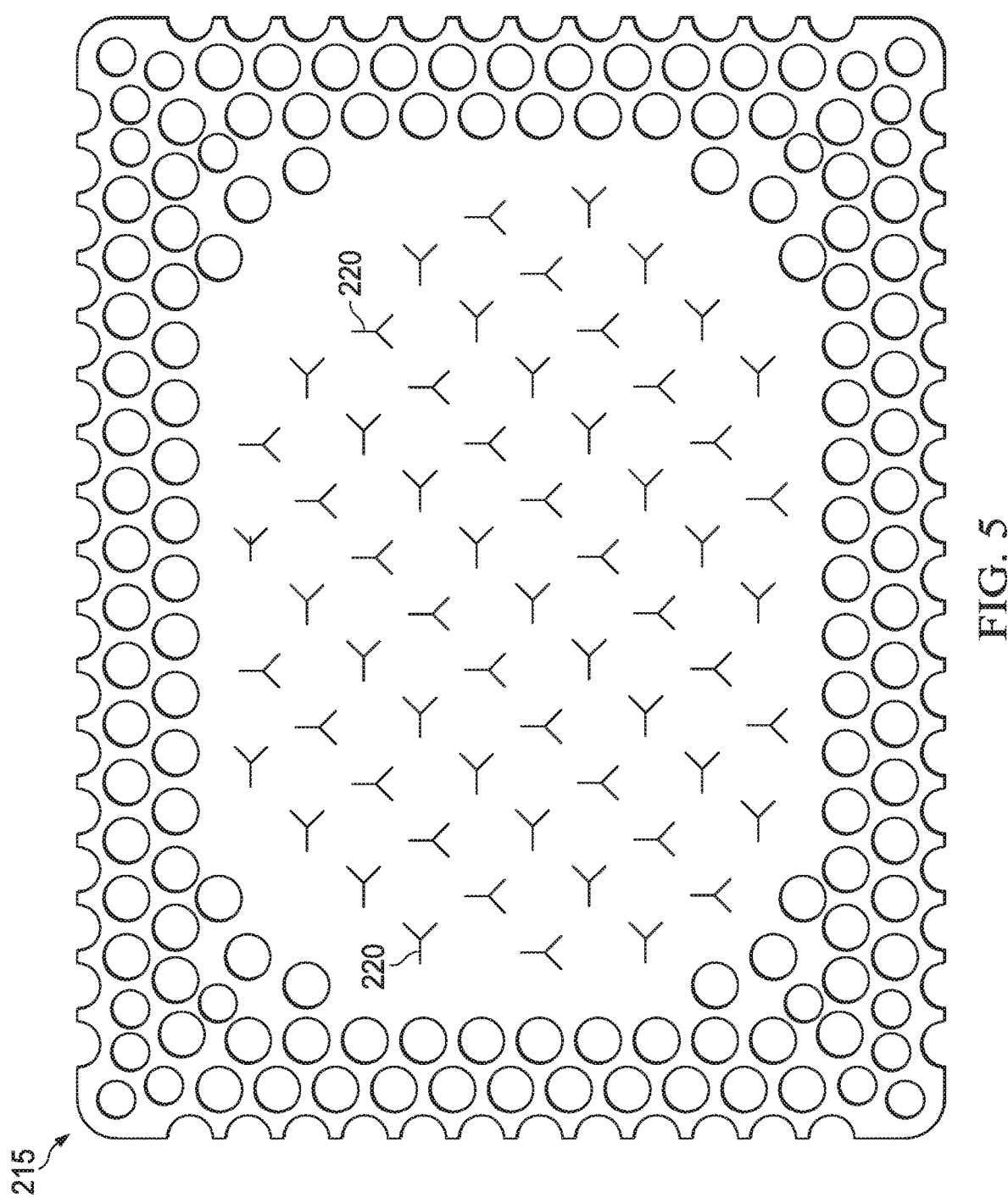
Figure 6:
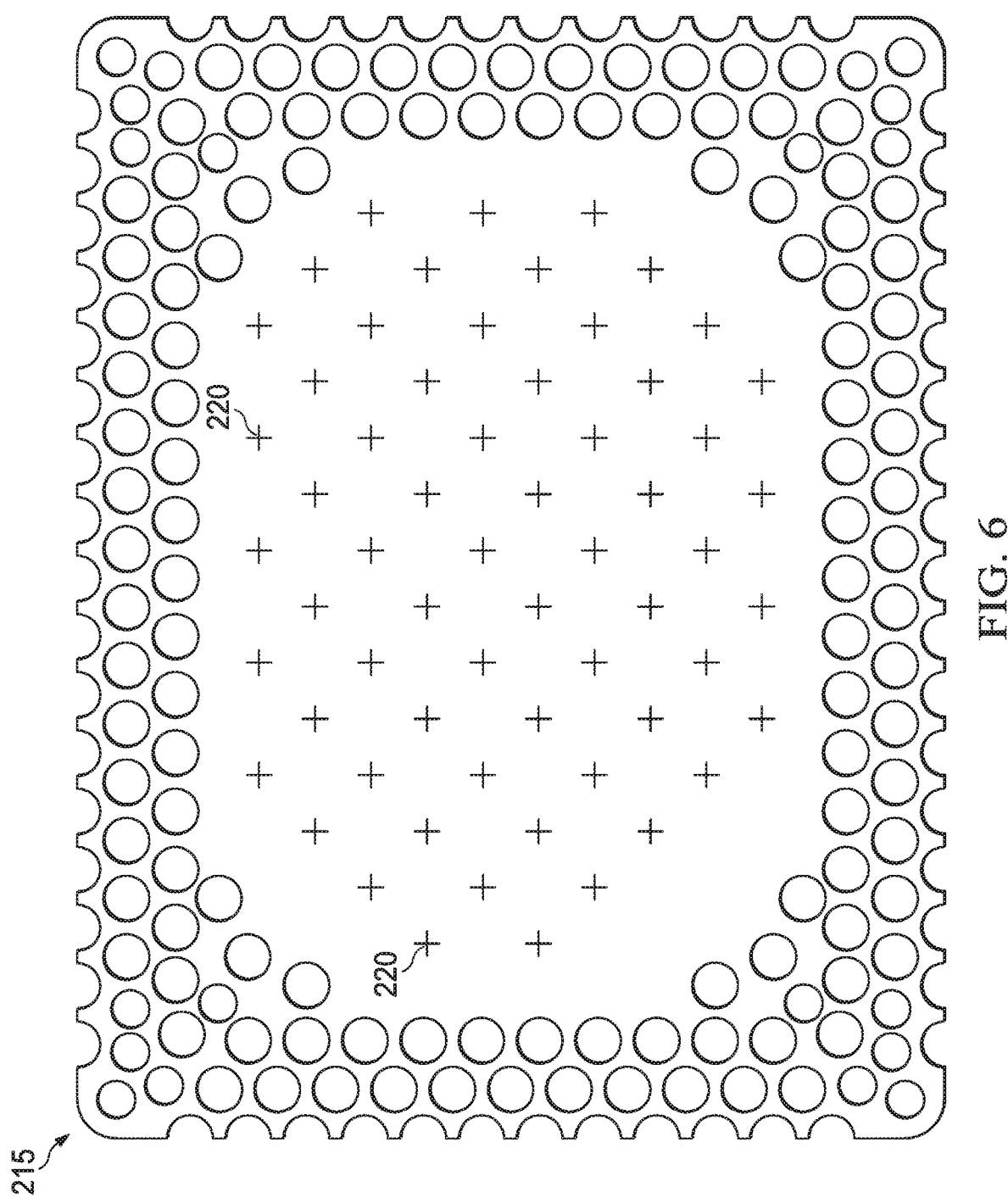

FIGS. 4-6 illustrate other example configurations of the fluid restrictions 220 in the second layer 215, in which the fluid restrictions 220 each generally comprise a combination of intersecting slits or cross-slits surrounded by optional apertures 235 in the periphery 225.

(ii) Apertures

The apertures 235 may be formed by cutting or by application of local RF or ultrasonic energy, for example, or by other suitable techniques for forming an opening. The apertures 235 may have a uniform distribution pattern, or may be randomly distributed on the periphery 225. The apertures 235 in the second layer 215 may have many shapes, including circles, squares, stars, ovals, polygons, slits, complex curves, rectilinear shapes, triangles, for example, or may have some combination of such shapes.

Each of the apertures 235 may have uniform or similar geometric properties. For example, in some embodiments, each of the apertures 235 may be circular apertures, having substantially the same diameter. In some embodiments, the diameter of each of the apertures 235 may be about 1 millimeter to about 50 millimeters. In other embodiments, the diameter of each of the apertures 235 may be about 1 millimeter to about 20 millimeters.

In other embodiments, geometric properties of the apertures 235 may vary. For example, the diameter of the apertures 235 may vary depending on the position of the apertures 235 in the second layer 215, as illustrated in FIG. 2. For example, in some embodiments, the apertures 235 disposed in the periphery 225 may have a diameter between about 9.8 millimeters to about 10.2 millimeters. In some embodiments, the apertures 235 disposed in the corners 240 may have a diameter between about 7.75 millimeters to about 8.75 millimeters.

At least one of the apertures 235 in the periphery 225 of the second layer 215 may be positioned at the edges 245 of the periphery 225, and may have an interior cut open or exposed at the edges 245 that is in fluid communication in a lateral direction with the edges 245. The lateral direction may refer to a direction toward the edges 245 and in the same plane as the second layer 215. As shown in the example of FIG. 2, the apertures 235 in the periphery 225 may be positioned proximate to or at the edges 245 and in fluid communication in a lateral direction with the edges 245. The apertures 235 positioned proximate to or at the edges 245 may be spaced substantially equidistant around the periphery 225 as shown in the example of FIG. 2. Alternatively, the spacing of the apertures 235 proximate to or at the edges 245 may be irregular.

C. Cover

In some embodiments, the dressing 104 includes a cover 116 which may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, Calif.; polyether block polyamide copolymer (PEBAX), for example, from Arkema, France; Inspire 2327; or other appropriate material.

D. Attachment Mechanism

In additional embodiments, the dressing 104 can include a means for attaching the cover 116 to an attachment surface, such as undamaged epidermis, a gasket, or another cover. The attachment mechanism may take many forms. For example, a medically-acceptable, pressure-sensitive adhesive can be used to bond the cover 116 to epidermis around a tissue site, such as a surface wound. Example adhesives include an acrylic adhesive, a paste, a hydrocolloid, a hydrogel, a silicone gel, or an organogel. The adhesive may have a coating weight between 25-65 grams per square meter (g.s.m.). Thicker adhesives, or combinations of adhesives, may be applied in some embodiments to improve the seal and reduce leaks.

In the example of FIG. 2, the dressing 104 includes an adhesive 255. The adhesive 255 may extend about a periphery, a portion, or the entire cover 116. In some embodiments, such a layer of the adhesive 255 may be continuous or discontinuous. Discontinuities in the adhesive 255 may be provided by apertures or holes (not shown) in the adhesive 255. The apertures or holes in the adhesive 255 may be formed after application of the adhesive 255 or by coating the adhesive 255 in patterns on a carrier layer, such as, for example, a side of the cover 116. Apertures or holes in the adhesive 255 may also be sized to enhance the MVTR of the dressing 104 in some example embodiments.

Additionally or alternatively, the attachment mechanism may be a device such as double-sided tape or a transfer adhesive.

E. Release Liner

Additionally, and as illustrated in the example of FIG. 2, the dressing 104 may include a release liner 260 attached to or positioned adjacent to the second layer 215 to protect the adhesive 255 prior to use. The release liner 260 may also provide stiffness to assist with, for example, deployment of the dressing 104. The release liner 260 may be, for example, a casting paper, a film, or polyethylene. Further, in some embodiments, the release liner 260 may be a polyester material such as polyethylene terephthalate (PET), or similar polar semi-crystalline polymer. The use of a polar semi-crystalline polymer for the release liner 260 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. In some embodiments, the release liner 260 may have a surface texture that may be imprinted on an adjacent layer, such as the second layer 215. Further, a release agent may be disposed on a side of the release liner 260 that is configured to contact the second layer 215. For example, the release agent may be a silicone coating and may have a release factor suitable to facilitate removal of the release liner 260 by hand and without damaging or deforming the dressing 104. In some embodiments, the release agent may be a fluorocarbon or a fluorosilicone, for example. In other embodiments, the release liner 260 may be uncoated or otherwise used without a release agent.

In further embodiments, a wound dressing provided herein comprises or consists essentially of a first layer 205, a second layer 215, a cover 116 and a release liner 260. In some embodiments, no additional layers, such as a film layer, are provided in the wound dressing or provided in between the first layer 205 and the second layer 215.

F. Additional Components

In yet further embodiments, additional components may be added to the wound dressings described herein. For example, one or more of the components of the dressing 104 may be treated with an antimicrobial agent and/or an antimicrobial agent may be present, for example, as a layer, in the dressing. In one example, the first layer 205 may be a foam, mesh, or non-woven substrate coated with an antimicrobial agent. In some embodiments, the first layer may comprise antimicrobial elements, such as fibers coated with an antimicrobial agent. Additionally or alternatively, some embodiments of the second layer 215 may be a polymer coated or mixed with an antimicrobial agent. In other examples, the fluid conductor 265 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, citric acid or a combination of these materials.

In further embodiments, a filler may also be disposed between a tissue site and the second layer 215. For example, if the tissue site is a surface wound, a wound filler may be applied interior to the periwound, and the second layer 215 may be disposed over the periwound and the wound filler. In some embodiments, the filler may be a manifold, such as open cell foam. The filler may comprise or consist essentially of the same material as the first layer 205 in some embodiments.

III. Methods of Manufacturing

Additionally, methods of manufacturing the dressings described herein are also provided. In some embodiments, a first curing step is performed to form the second layer 215, for example a silicone, a polyurethane, a hydrocolloid, an acrylic or a polyolefinic material can be initially cured to form the second layer 215, for example a silicone gel layer. The methods of manufacturing may optionally include a pre-step of applying the material, such as silicone for example, to a substrate, such as a woven, non-woven, molded, or extruded mesh, or a film, prior to the first curing step. A second curing step, also called a local curing step, can then be performed to advance the cure at desired perforation locations, for example where the slits and/or slots will be located, on the second layer 215. The second layer 215 may then be perforated at the perforation locations to form a plurality of fluid restrictions 220, as discussed above, through the second layer 215.

Without being bound by theory, the second, localized curing step cross-links the gel at the desired perforation locations to form a soft and less tacky elastomer allowing the fluid restrictions 220 to open and close when in use. In some embodiments, tack of the second layer 215 at the perforation locations, for example, at about 0.25 mm to about 1.5 mm on either side of the slit or slot (the longer length side) is at least 10%, 20%, 30%, 40%, 50%, 60%, 70%, 80%, 90%, 95% or 99% less tacky than the remaining second layer 215 and/or the second layer 215 following the first curing step. In other embodiments, the second localized curing step eliminates tack (i.e. tack equals zero) at the perforation locations, for example from about 0.25 mm to about 1.5 mm on either side of the slit or slot (the longer length side). Additionally or alternatively, in some embodiments about 0.25 mm to about 1.5 mm on either side of the slit or slot (the longer length side) has a hardness less than about 5 Shore 00. Tack can be measured by standard methods known in the art, such as BS EN1719, ASTM D3121 and ASTM D2979. Hardness can be measured by standard methods known in the art, such as ASTM D2240 and ISO 7619-1.

In one embodiment, a method of manufacturing a dressing for negative pressure treatment comprises:

a first curing step comprising curing silicone, polyurethane, a hydrocolloid, acrylic or a polyolefinic material to form a gel layer;

a second curing step comprising locally curing the gel layer at perforation locations on the gel layer;

perforating the gel layer at the perforation locations to form a plurality of fluid restrictions through the gel layer; and assembling a polymer drape, a manifold layer (e.g. the first layer) and the gel layer (e.g. the second layer) in a stacked configuration, wherein the manifold layer is interposed between the polymer drape and the gel layer.

In a particular embodiment, the gel layer (e.g. the second layer) is a silicone gel layer that has been previously applied to a substrate.

Various types of curing can be used for the first and the second curing steps. For example, an addition cure (such as a platinum cure), a free radical cure (such as a peroxide cure), an ionizing radiation cure (such as ultraviolet (UV) light, gamma rays, x-rays, and e-beam), a condensation cure or a combination thereof may be used for the first and/or the second curing steps. In some embodiments, the first curing step and the second curing step may be performed using the same type of cure. In particular embodiments, a UV cure is used for the first curing step, and even more particularly a UV cure can be used for both the first and the second curing steps. The UV light can be applied in the second curing step at the desired perforation locations. Alternatively, the first curing step and the second curing step may be performed using different cure types. For example, a dual-cure system may be used in which the first cure is done using an addition cure, such as a platinum or moisture cure system, and the second cure is done with a UV cure system, or vice versa. Blending different cure types may provide extra stability to the second layer 215.

Additionally or alternatively, localized heating from lasers and/or a narrow focused e-beam can be used to advance the cure (i.e. the second curing step). For example heat cure systems using peroxide cross-linked formulas may be used to provide the local cure at the desired perforation locations.

In some embodiments, a material, device, layer or mechanism can be used to limit the second cure to the desired perforation locations. For example, a shielding or blocking material can be used such as, an opaque layer. The opaque layer may be a printed pattern or a polymeric film mesh on or adjacent to the second layer 215 to block ionizing radiation such as UV light. Additionally or alternatively, radio opaque materials such as metal films can be used to block ionizing radiation such as gamma rays, x-rays and e-beam. E-beam and x-rays may also be deflected or rastered using cathode ray technology to give the required pattern.

In some embodiments, an accelerator rich pre-polymer may be applied to the second layer 215 prior to the second curing step. In further embodiments, the accelerator rich pre-polymer is applied to perforation locations on the second layer 215. Examples of accelerator rich pre-polymers include platinum and rhodium.

In further embodiments, the methods of manufacturing the dressing 104 include assembling the individual components, such as the cover 116 (e.g. polymer drape), the first layer 205 (e.g. the manifold layer) and the second layer 215 (e.g. the silicone gel layer) in a stacked configuration, wherein the first layer 205 is interposed between the cover 116 and the second layer 215.

Individual components of the dressing 104 may be bonded or otherwise secured to one another with a solvent or non-solvent adhesive, or with thermal welding, for example, without adversely affecting fluid management. Further, the first layer 205 may be coupled to the interior border 250 of the second layer 215 in any suitable manner, such as with a weld or an adhesive, for example.

IV. Methods of Use

The dressings provided herein are useful in negative pressure therapy. As shown in the example of FIG. 2, the dressing interface 270 may disposed over the aperture 275 and attached to the cover 116. The fluid conductor 265 may be a flexible tube, which can be fluidly coupled on one end to the dressing interface 270 and to the negative-pressure source 102. The dressing interface 270 may be an elbow connector, as shown in the example of FIG. 2, which can be placed over an aperture 275 in the cover 116 to provide a fluid path between the fluid conductor 265 and the tissue interface 114.

In operation, the tissue interface 114 may be placed within, over, on, or otherwise proximate to a tissue site. If the tissue site is a wound, for example, the tissue interface 114 may partially or completely fill the wound, or may be placed over the wound. The cover 116 may be placed over the tissue interface 114 and sealed to an attachment surface near a tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment. Negative pressure applied across the tissue site through the tissue interface 114 in the sealed therapeutic environment can induce macrostrain and micro-strain in the tissue site, as well as remove exudates and other fluids from the tissue site, which can be collected in container 106.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Negative pressure applied through the tissue interface 114 can create a negative pressure differential across the fluid restrictions 220 in the second layer 215, which can open or expand the fluid restrictions 220 from their resting state. For example, in some embodiments in which the fluid restrictions 220 may comprise substantially closed fenestrations through the second layer 215, a pressure gradient across the fenestrations can strain the adjacent material of the second layer 215 and increase the dimensions of the fenestrations to allow liquid movement through them, similar to the operation of a duckbill valve. Opening the fluid restrictions 220 can allow exudate and other liquid movement through the fluid restrictions 220 into the first layer 205 and the container 106. Changes in pressure can also cause the first layer 205 to expand and contract, and the interior border 250 may protect the epidermis from irritation. The second layer 215 can also substantially reduce or prevent exposure of tissue to the first layer 205, which can inhibit growth of tissue into the first layer 205.

If the negative-pressure source 102 is removed or turned-off, the pressure differential across the fluid restrictions 220 can dissipate, allowing the fluid restrictions 220 to move to their resting state and prevent or reduce the rate at which exudate or other liquid from returning to the tissue site through the second layer 215.

In some embodiments, the first layer 205 may be hydrophobic to minimize retention or storage of liquid in the dressing 104. In other embodiments, the first layer 205 may be hydrophilic. In an example in which the first layer 205 may be hydrophilic, the first layer 205 may also wick fluid away from a tissue site, while continuing to distribute negative pressure to the tissue site. The wicking properties of the first layer 205 may draw fluid away from a tissue site by capillary flow or other wicking mechanisms, for example. An example of a hydrophilic first layer 205 is a polyvinyl alcohol, open-cell foam such as used in V.A.C. WHITE-FOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the second layer 215, which can open or expand the fluid restrictions 220 from their resting state to allow the instillation solution or other fluid to be distributed to the tissue site.

Also provided herein are methods of treating a surface wound to promote healing and tissue granulation. The methods may include applying the dressing 104 to a surface wound and sealing the dressing 104 to epidermis adjacent to the surface wound. For example, the second layer 215 may be placed over the surface wound, covering at least a portion of the edge of the surface wound and a periwound adjacent to the surface wound. The cover 116 may also be attached to epidermis around the second layer 215. The dressing 104 may be fluidly coupled to a negative-pressure source, such as the negative-pressure source 102. Negative pressure from the negative-pressure source may be applied to the dressing 104, opening the fluid restrictions 220. The fluid restrictions 220 can be closed by blocking, stopping, or reducing the negative pressure. The second layer 215 can substantially prevent exposure of tissue in the surface wound to the first layer 205, inhibiting growth of tissue into the first layer 205. The dressing 104 can also substantially prevent maceration of the periwound.

Additionally, the cover 116, the first layer 205, the second layer 215, or various combinations may be assembled before application or in situ. For example, the cover 116 may be laminated to the first layer 205, and the second layer 215 may be laminated to the first layer 205 opposite the cover 116 in some embodiments. In some embodiments, one or more layers of the tissue interface 114 may be coextensive. In some embodiments, the dressing 104 may be provided as a single, composite dressing. For example, the second layer 215 may be coupled to the cover 116 to enclose the first layer 205, wherein the second layer 215 is configured to face a tissue site.

In use, the release liner 260 (if included) may be removed to expose the second layer 215, which may be placed within, over, on, or otherwise proximate to a tissue site, particularly a surface tissue site and adjacent epidermis. The second layer 215 may be interposed between the first layer 205 and the tissue site, which can substantially reduce or eliminate adverse interaction with the first layer 205. For example, the second layer 215 may be placed over a surface wound (including edges of the wound) and undamaged epidermis to prevent direct contact with the first layer 205. Treatment of a surface wound or placement of the dressing 104 on a surface wound includes placing the dressing 104 immediately adjacent to the surface of the body or extending over at least a portion of the surface of the body. Treatment of a surface wound does not include placing the dressing 104 wholly within the body or wholly under the surface of the body, such as placing a dressing within an abdominal cavity. In some applications, the interior portion 230 of the second layer 215 may be positioned adjacent to, proximate to, or covering a tissue site. The periphery 225 of the second layer 215 may be positioned adjacent to or proximate to tissue around or surrounding the tissue site. The second layer 215 may be sufficiently tacky to hold the dressing 104 in position, while also allowing the dressing 104 to be removed or re-positioned without trauma to the tissue site.

Removing the release liner 260 can also expose the adhesive 255, and the cover 116 may be attached to an attachment surface. For example, the cover may be attached to epidermis peripheral to a tissue site, around the first layer 205. The adhesive 255 may be in fluid communication with an attachment surface through the apertures 235 in at least the periphery 225 of the second layer 215 in some embodiments. The adhesive 255 may also be in fluid communication with the edges 245 through the apertures 235 exposed at the edges 245.

Once the dressing 104 is in the desired position, the adhesive 255 may be pressed through the apertures 235 to bond the dressing 104 to the attachment surface. The apertures 235 at the edges 245 may permit the adhesive 255 to flow around the edges 245 for enhancing the adhesion of the edges 245 to an attachment surface.

In some embodiments, apertures 235 in the second layer 215 may be sized to control the amount of the adhesive 255 in fluid communication with the apertures 235. For a given geometry of the corners 240, the relative sizes of the apertures 235 may be configured to maximize the surface area of the adhesive 255 exposed and in fluid communication through the apertures 235 at the corners 240. For example, as shown in FIG. 2, the edges 245 may intersect at substantially a right angle, or about 90 degrees, to define the corners 240. In some embodiments, the corners 240 may have a radius of about 10 millimeters. Further, in some embodiments, three of the apertures 235 having a diameter between about 7.75 millimeters to about 8.75 millimeters may be positioned in a triangular configuration at the corners 240 to maximize the exposed surface area for the adhesive 255. In other embodiments, the size and number of the apertures 235 in the corners 240 may be adjusted as necessary, depending on the chosen geometry of the corners 240, to maximize the exposed surface area of the adhesive 255. Further, the apertures 235 at the corners 240 may be fully housed within the second layer 215, substantially precluding fluid communication in a lateral direction exterior to the corners 240. The apertures 235 at the corners 240 being fully housed within the second layer 215 may substantially preclude fluid communication of the adhesive 255 exterior to the corners 240, and may provide improved handling of the dressing 104 during deployment at a tissue site. Further, the exterior of the corners 240 being substantially free of the adhesive 136 may increase the flexibility of the corners 240 to enhance comfort.

In some embodiments, the bond strength of the adhesive 255 may vary in different locations of the dressing 104. For example, the adhesive 255 may have lower bond strength in locations adjacent to the second layer 215 where the apertures 235 are relatively larger, and may have higher bond strength where the apertures 235 are smaller. Adhesive 255 with lower bond strength in combination with larger apertures 235 may provide a bond comparable to adhesive 255 with higher bond strength in locations having smaller apertures 235.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the second layer 215 to enhance the movement and proliferation of epithelial cells at a tissue site and reduce the likelihood of granulation tissue in-growth.

Thus, the dressing 104 can provide a sealed therapeutic environment proximate to a tissue site, substantially isolated from the external environment, and the negative-pressure source 102 can reduce the pressure in the sealed therapeutic environment. The second layer 215 may provide an effective and reliable seal against challenging anatomical surfaces, such as an elbow or heel, at and around a tissue site. Further, the dressing 104 may permit re-application or re-positioning, to correct air leaks caused by creases and other discontinuities in the dressing 104, for example. The ability to rectify leaks may increase the efficacy of the therapy and reduce power consumption in some embodiments.

The systems, apparatuses, and methods described herein may provide significant advantages over prior dressings. For example, some dressings for negative-pressure therapy can require time and skill to be properly sized and applied to achieve a good fit and seal. In contrast, some embodiments of the dressing 104 provide a negative-pressure dressing that is simple to apply, reducing the time to apply and remove. In some embodiments, for example, the dressing 104 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, protection of the peripheral tissue from maceration, and a low-trauma and high-seal bond. These characteristics may be particularly advantageous for surface wounds having moderate depth and medium-to-high levels of exudate. Some embodiments of the dressing 104 may remain on the tissue site for at least 5 days, and some embodiments may remain for at least 7 days. Antimicrobial agents in the dressing 104 may extend the usable life of the dressing 104 by reducing or eliminating infection risks that may be associated with extended use, particularly use with infected or highly exuding wounds.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
    a first layer coupled to a second layer, wherein the second layer comprises a gel and a plurality of fluid restrictions through the second layer that are configured to expand in response to a pressure gradient across the second layer, and wherein a first portion of the gel on opposing sides of at least one of the plurality of fluid restrictions has a localized cure such that the first portion of the gel is less tacky than a second portion of the gel at another location of the second layer; and
    a polymer drape coupled to the first layer;
    wherein the first layer is interposed between the second layer and the polymer drape.

2. The dressing of claim 1, wherein the first layer comprises a manifold layer and the second layer comprises a silicone gel layer.

3. The dressing of claim 1, where the second layer has a substantially flat configuration, and one or more of the following:
    a density of less than 300 g/m$^2$;
    a hardness between and including about 5 Shore OO and about 80 Shore OO; and
    a thickness between and including about 200 μm and about 1000 μm.

4. The dressing of claim 1, wherein the fluid restrictions in the second layer comprise slits or slots having a length less than 4 mm and a width less than 1 mm.

5. The dressing of claim 4, wherein the length is less than 3 mm and the width is less than 1 mm.

6. The dressing of claim 4, wherein the width is at least 0.5 mm and the length is at least 2 mm.

7. The dressing of claim 1, wherein the second layer allows the fluid restrictions to open and close when in use, and wherein the first portion of the gel is at the opposing sides of at least one of the plurality of fluid restrictions.

8. The dressing of claim 7, wherein about 0.25 mm to about 1.5 mm on a longer length side of fluid restrictions is at least 10% less tacky than the remaining second layer.

9. The dressing of claim 7, wherein about 0.25 mm to about 1.5 mm on a longer length side of the fluid restrictions has a hardness less than about 5 Shore OO.

10. The dressing of claim 1, wherein the fluid restrictions are distributed across the second layer in a uniform pattern.

11. The dressing of claim 10, wherein the uniform pattern comprises a grid of parallel rows and columns.

12. The dressing of claim 1, wherein:
    the fluid restrictions are distributed across the second layer in parallel rows and columns;
    the rows are spaced about 3 mm on center; and
    the fluid restrictions in each of the rows are spaced about 3 mm on center.

13. The dressing of claim 1, wherein the fluid restrictions in adjacent rows are offset.

14. The dressing of claim 1, wherein the fluid restrictions comprise elastomeric valves in the second layer that are normally closed.

15. The dressing of claim 14, wherein the elastomeric valves are fenestrations.

16. The dressing of claim 1, wherein the first layer comprises foam.

17. The dressing of claim 16, wherein the foam is reticulated.

18. The dressing of claim 17, wherein the foam is reticulated and has a free volume of at least 90%.

19. The dressing of claim 16, wherein the foam is porous and has an average pore size in a range of 400-600 μm.

20. The dressing of claim 16, wherein the first layer has a thickness less than 7 mm.

21. The dressing of claim 1, wherein the first layer is hydrophobic.

22. The dressing of claim 1, wherein the fluid restrictions are coextensive with the first layer.

23. The dressing of claim 1, wherein the polymer drape comprises a fluid port configured to be coupled to a fluid conductor.

24. The dressing of claim 1, further comprising an adhesive and a release liner.

25. A method of treating a surface wound with negative pressure, the method comprising:
    applying the dressing of claim 1 to the surface wound;
    sealing the dressing to epidermis adjacent to the surface wound;

fluidly coupling the dressing to a negative-pressure source; and applying negative pressure from the negative-pressure source to the dressing and promoting healing and tissue granulation.

26. The method of claim 25, wherein the second layer is exposed to the tissue site during the step of applying negative pressure.

27. The method of claim 25, wherein applying the dressing comprises disposing at least part of the dressing across an edge of the surface wound.

28. The method of claim 25, wherein applying negative pressure opens the fluid restrictions in the second layer.

29. The method of claim 28, further comprising reducing negative pressure from the negative-pressure source, wherein reducing negative pressure closes the fluid restrictions in the second layer.

30. The method of claim 25, further comprising fluidly coupling a fluid container between the dressing and the negative-pressure source, and transferring exudate from the dressing to the fluid container.

\* \* \* \* \*